US008710267B2

(12) United States Patent
Stroefer et al.

(10) Patent No.: US 8,710,267 B2
(45) Date of Patent: Apr. 29, 2014

(54) PROCESS FOR PREPARING MDA VIA THE STAGE OF THE AMINAL

(75) Inventors: Eckhard Stroefer, Mannheim (DE); Kai Thiele, Antwerpen (BE); Michael Zoellinger, Eislingen (DE); Johnny Moors, Baton Rouge, LA (US); Jon S. Speier, Baton Rouge, LA (US)

(73) Assignee: BASF SE, Ludwigshafen (DE)

( * ) Notice: Subject to any disclaimer, the term of this patent is extended or adjusted under 35 U.S.C. 154(b) by 31 days.

(21) Appl. No.: 13/265,271

(22) PCT Filed: Apr. 19, 2010

(86) PCT No.: PCT/EP2010/055126
§ 371 (c)(1),
(2), (4) Date: Oct. 19, 2011

(87) PCT Pub. No.: WO2010/121990
PCT Pub. Date: Oct. 28, 2010

(65) Prior Publication Data
US 2012/0035396 A1 Feb. 9, 2012

(30) Foreign Application Priority Data
Apr. 20, 2009 (EP) .................................... 09158207

(51) Int. Cl.
*C07C 211/00* (2006.01)
*C09B 11/02* (2006.01)
(52) U.S. Cl.
USPC .......................................... 564/333; 564/332
(58) Field of Classification Search
None
See application file for complete search history.

(56) References Cited

U.S. PATENT DOCUMENTS

| 5,196,591 | A | 3/1993 | Knofel et al. |
|---|---|---|---|
| 2004/0092772 | A1 | 5/2004 | Perego et al. |
| 2005/0174064 | A1 | 8/2005 | Agostinelli et al. |
| 2006/0084827 | A1 | 4/2006 | Stroefer et al. |
| 2006/0185513 | A1 | 8/2006 | Stroefer et al. |
| 2006/0211841 | A1 | 9/2006 | Stroefer et al. |
| 2007/0135660 | A1 | 6/2007 | Rumpf et al. |
| 2010/0217035 | A1 | 8/2010 | Knoesche et al. |
| 2010/0270140 | A1 | 10/2010 | Siegert et al. |
| 2010/0324311 | A1 | 12/2010 | Siegert et al. |

FOREIGN PATENT DOCUMENTS

| EP | 0 509 309 | 10/1992 |
|---|---|---|
| EP | 1 063 221 | 12/2000 |
| EP | 1 616 890 | 1/2006 |
| JP | 2004 300085 | 10/2004 |
| WO | 01 97969 | 12/2001 |
| WO | 2004 078678 | 9/2004 |
| WO | 2004 078690 | 9/2004 |
| WO | 2004 078691 | 9/2004 |
| WO | 2005 077877 | 8/2005 |
| WO | 2009 027416 | 3/2009 |
| WO | 2009 037179 | 3/2009 |
| WO | 2009 047109 | 4/2009 |
| WO | 2009 077416 | 6/2009 |

OTHER PUBLICATIONS

Eberhardt, C., et al., "Ueber einige Condensationsproducte aromatischer Amine mit Formaldehyd in alkalischer Loesung," Berichte der Deutschen chemischen Gesellschaft, Verlag Chemie, vol. 27, No. 2, pp. 1804-1815, (Jan. 1, 1894) XP007915041.
International Search Report Issued Oct. 29, 2010 in PCT/EP10/055126 Filed Apr. 19, 2010.
U.S. Appl. No. 13/266,049, filed Oct. 24, 2011, Stroeffer, et al.
U.S. Appl. No. 13/163,928, filed Jun. 20, 2011, Rosendahl, et al.

*Primary Examiner* — Clinton Brooks
(74) *Attorney, Agent, or Firm* — Oblon, Spivak, McClelland, Maier & Neustadt, L.L.P.

(57) ABSTRACT

The invention relates to a process for preparing methylenediphenyldiamine (MDA), comprising the following steps a) to c):
  a) converting formaldehyde and aniline to aminal
  b) removing water from the aminal obtained in step a) to establish a water content of 0 to 5% by weight based on the aminal, and
  c) adding an acidic catalyst to the aminal having a water content of 0 to 5% by weight,
which comprises
using formaldehyde in step a) in the form of highly concentrated formaldehyde with a $CH_2O$ content of >50% by weight and preparing the formaldehyde by oxidative dehydrogenation from methanol.

15 Claims, No Drawings

PROCESS FOR PREPARING MDA VIA THE STAGE OF THE AMINAL

CROSS REFERENCE TO RELATED APPLICATIONS

The present application is a 35 U.S.C. §371 national stage patent application of International patent application PCT/EP10/055,126, filed on Apr. 19, 2010, the text of which is incorporated by reference, and claims the benefit of the filing date of European application no. EP09158207.2, filed on Apr. 20, 2009, the text of which is also incorporated by reference.

The invention relates to a process for preparing methylenediphenyldiamine (MDA), wherein formaldehyde and aniline are first converted to aminal. After at least partial removal of water, an acidic catalyst is added to the aminal to obtain MDA. Formaldehyde is used in highly concentrated form with a $CH_2O$ content of >50% by weight, the formaldehyde being prepared by oxidative dehydrogenation from methanol.

MDA is a representative of the polyamines of the diphenylmethane series. MDA is especially used as an intermediate from which the corresponding polyisocyanate (MDI) is synthesized by phosgenation. Processes for preparing MDA have been known for sometime. EP-A 1 616 890 gives an overview of MDA preparation processes. Typically, the preparation is effected by converting aniline and formaldehyde in the presence of acidic catalysts (acidic condensation). Depending on the time of catalyst addition, the condensation of aniline and formaldehyde can proceed in different reaction steps.

In the absence of an acidic catalyst, formaldehyde first condenses with aniline to form aminal and water. The rearrangement of the aminal to MDA proceeds in two stages, a first step involving rearrangement to para- or ortho-aminobenzylaniline under acid catalysis. The aminobenzylanilines are rearranged to MDA in a second step. Main products of the acid-catalyzed reaction of aniline and formaldehyde are the diamine 4,4'-MDA, its positional isomers 2,4'-MDA and 2,2'-MDA, and higher homologous polyamines of the diphenylmethane series.

In the presence of an acidic catalyst, aniline and formaldehyde directly form the aminobenzylanilines, which subsequently react further to give the bicyclic MDA isomers and higher polycyclic MDA homologs.

In the acid-catalyzed MDA preparation process described in EP-A 1 616 890, aniline and formaldehyde are first converted in such a way that a water content of <20% by weight and a degree of protonation of <15% are established in the acidic reaction mixture. When the ratio of the proportions by weight of p-aminobenzylaniline to 4,4'-MDA in the acidic reaction mixture goes below a value of 1, the reaction temperature is increased. In one embodiment, the process is performed with formation of aminal as an intermediate compound and subsequent addition of the acidic catalyst, in which case the water can first be removed at least partly from the aminal after the conversion to the aminal.

EP-B 1 063 221 relates to a process for reacting a solution with at least one further chemical compound. The solution comprises a mixture of at least two chemical compounds in a chemical equilibrium with one another, and may be an aqueous formaldehyde solution. Excluded, however, is the reaction of a formaldehyde solution which comprises polyoxymethylene glycols and optionally monomeric formaldehyde and/or methylene glycol with aniline in the presence of an acidic catalyst.

WO 2004/078678 relates to a process for preparing highly concentrated formaldehyde solution with a $CH_2O$ content of ≥50% by weight. The reactant used is an aqueous formaldehyde solution with a low $CH_2O$ content, a portion of this solution being evaporated (partial evaporation). This involves heating the aqueous formaldehyde solution to an evaporation temperature at which water is enriched in the gas phase relative to the liquid phase, and the gas phase formed is drawn off continuously or discontinuously.

A further process for preparing highly concentrated formaldehyde solutions is described in WO 2005/077877, according to which water is removed from a lower-concentration formaldehyde solution with a formaldehyde content between 5 and 50% by weight. This involves feeding the low-concentration formaldehyde solution to a preheater and heating it therein, then decompressing it by means of a pressure-retaining device and concentrating it in a helical tube evaporator.

WO 2004/078691 relates to a process for thermally stabilizing highly concentrated formaldehyde solutions with a formaldehyde content of <70% by weight against precipitation of solids. This involves heating the highly concentrated formaldehyde solution immediately after preparation thereof with a specific heating rate to temperatures of 80 to 200° C. and then storing it in this temperature range.

WO 2004/078690 relates to a process for providing highly concentrated gaseous formaldehyde with a molar formaldehyde to water ratio of ≥0.6. In this process, at least a portion of an aqueous formaldehyde solution is first evaporated off, by heating the aqueous formaldehyde solution to an evaporation temperature and drawing off the gas phase formed.

It is an object of the present invention to provide an economically viable process for preparing MDA, forming aminal as an intermediate.

The object is achieved by a process for preparing methylenediphenyldiamine (MDA), comprising the following steps a) to c):
  a) converting formaldehyde and aniline to aminal
  b) removing water from the aminal obtained in step a) to establish a water content of 0 to 5% by weight based on the aminal, and
  c) adding an acidic catalyst to the aminal having a water content of 0 to 5% by weight,
which comprises
using formaldehyde in step a) in the form of highly concentrated formaldehyde with a $CH_2O$ content of >50% by weight and preparing the formaldehyde by oxidative dehydrogenation from methanol.

The process according to the invention has the advantage that the use of highly concentrated formaldehyde results in a lower water content being present in the system, especially in step a). Commercially available formaldehyde is normally in the form of an aqueous formaldehyde solution with a total concentration of approx. 20 to 30% by weight of formaldehyde ($CH_2O$ content). The remaining percentages by weight of such a commercially available aqueous formaldehyde solution result principally from the water. Thus, in the case of use of such commercially available aqueous formaldehyde solutions, a large amount of water is introduced into the MDA synthesis together with the formaldehyde. However, this water is generally not required in the synthesis; instead, the conversion of formaldehyde and aniline releases water, such that the addition of a large amount of water in principle has an adverse effect on the MDA formation.

Secondly, relatively highly concentrated aqueous formaldehyde solutions are relatively unstable, such that they relatively rapidly become turbid owing to precipitates in the course of storage at room temperature. Consequently, owing to these stability problems on the industrial scale, commercially available aqueous formaldehyde solutions with a relatively low $CH_2O$ content are frequently used in the MDA synthesis, and hence large amounts of water are inevitably introduced into the system. This high water burden, however, also determines the size of the reactors, the periphery thereof and the workup of the products. In addition, the excess water must be treated and disposed of as wastewater. Accordingly, it is highly advantageous that, in the process according to the invention, in step a), less water is introduced into the system owing to the use of highly concentrated formaldehyde. Consequently, in step b), only a relatively small amount of water need be removed, which, on the industrial scale, has a positive effect on the size of the reactors and the associated costs.

A further advantage of the process according to the invention is that the use of formaldehyde prepared by oxidative dehydrogenation, especially by rich oxidative dehydrogenation from methanol, results in less formic acid (by-product) being introduced into the process. The MDA prepared by the process according to the invention thus also has a higher purity.

Steps a) to c) of the process according to the invention are described in detail hereinafter.

In step a), formaldehyde and aniline are converted to aminal. Aminal is an intermediate in the preparation of MDA. Step a) is preferably performed in complete or virtually complete absence of an acidic catalyst. The molar ratio of aniline to formaldehyde is normally 1.5:1 to 6:1, preferably 1.8:1 to 5:1.

The temperature is normally 20 to 100° C., preferably 30 to 95° C., more preferably 40 to 90° C. In step a), preference is given to establishing a water content of <20% by weight and/or a degree of protonation of <15%.

In step a), formaldehyde is used in the form of highly concentrated formaldehyde with a $CH_2O$ content of >50% by weight, preferably 70% by weight, especially 80% by weight. Methods for preparing highly concentrated formaldehyde with a $CH_2O$ content of >50% by weight are known to those skilled in the art. According to the invention, formaldehyde which has been prepared by oxidative dehydrogenation from methanol is used. Preference is given to using formaldehyde which has been prepared by rich oxidative dehydrogenation. In this context, "rich" means that the molar ratio of methanol to oxygen in the feed to the formaldehyde synthesis corresponds to or exceeds the value of 2:1. Formaldehyde synthesis processes by oxidative dehydrogenation of methanol are known to those skilled in the art. The formaldehyde can be obtained directly as highly concentrated formaldehyde; normally, however, formaldehyde is first prepared with a lower $CH_2O$ content, from which, as described above, highly concentrated formaldehyde with a $CH_2O$ content of >50% by weight is obtained by methods known to those skilled in the art.

The highly concentrated formaldehyde can be used as an aqueous solution or in gaseous form.

In one embodiment of the present invention, the highly concentrated formaldehyde solution with a $CH_2O$ content of >50% by weight used in step a) is prepared from an aqueous formaldehyde solution with a lower $CH_2O$ content by evaporating a portion of this solution by heating the aqueous formaldehyde solution to an evaporation temperature at which the water is enriched in the gas phase relative to the liquid phase, and the gas phase formed is drawn off continuously or discontinuously.

Preference is given to heating the aqueous formaldehyde solution to an evaporation temperature T for which:

$$T[°C.] < T_{max}[°C.]$$

where $T_{max}(c) = A + B \times (c/100) + C \times (c/100)^2 + D \times (c/100)^3$ and $A = +68.759$, $B = +124.77$, $C = -12.851$, $D = -10.095$,
where c is the present $CH_2O$ content of the aqueous formaldehyde solution during the evaporation in % by weight and is from 20 to 99% by weight.

Preference is given to evaporating the aqueous formaldehyde solutions of this embodiment in a stirred tank, a helical tube, a film evaporator or another apparatus with heat exchanger characteristics. The pressure during the evaporation is preferably 0.1 to 50 bar.

In a further embodiment of the present invention, the highly concentrated formaldehyde solution with a $CH_2O$ content used in step a) is prepared from an aqueous formaldehyde solution with a lower $CH_2O$ content by supplying the aqueous formaldehyde solution with a lower $CH_2O$ content to a preheater, heating it in the preheater, decompressing it by means of a pressure-retaining device and concentrating it in a helical tube evaporator to obtain a vapor stream and the highly concentrated formaldehyde solution with a $CH_2O$ content of >50% by weight as the bottom stream.

Preferably, in this embodiment, the aqueous formaldehyde solution with a lower $CH_2O$ content is decompressed in the pressure-retaining device to give a biphasic mixture which is subsequently fed to the helical tube evaporator. In addition, a stripping gas and/or a stabilizer can be added to the biphasic mixture before it is fed into the helical tube evaporator. The stripping gas is preferably nitrogen; the stabilizer is preferably methanol, ethanol, a propanol, a butanol, urea or melamine.

Preferably, in the helical tube evaporator, suitable selection of the geometry thereof and of the operating conditions, especially of the total flow rate and of the gas content in the biphasic mixture passed through the helical tube evaporator, establishes a wavy film flow. In addition, it is advantageous to use devices for intensive mixing of the biphasic mixture in the helical tube evaporator, especially valves, throttles, ribs or wire knits. In addition, it is advantageous to partially or completely condense the vapor stream from the helical tube evaporator in a condenser, preferably a surface condenser, especially a quench condenser. Optionally, the condensed proportion of the vapor stream and/or the bottom stream from the helical tube evaporator can be entirely or partly recycled into the preheater.

In a further embodiment of the present invention, a highly concentrated formaldehyde solution with a $CH_2O$ content of >50% by weight used in step a) is stabilized against precipitation of solids by heating it immediately after preparation thereof with a heating rate of at least 5° C./min to a temperature of at least 80 to not more than 200° C. and storing it at a temperature in this range.

The heating rate is preferably at least 10° C./min and/or heating is effected to a temperature of at least 100 to not more than 150° C. The highly concentrated formaldehyde solution is preferably obtained from a formaldehyde solution of lower concentration in a film evaporator.

In a further embodiment of the present invention, gaseous highly concentrated formaldehyde with a $CH_2O$ content of >50% by weight and a molar $CH_2O$ to $H_2O$ ratio of ≥0.6 is used in step a), the gaseous highly concentrated formaldehyde being prepared by evaporating at least a portion of an aqueous formaldehyde solution.

Preferably, in this embodiment, the aqueous formaldehyde solution is heated to an evaporation temperature T and the gas phase formed is drawn off, where, for the evaporator temperature T:

$$T[°C.] \geq T'_{min}[°C.]$$

where $T'_{min}(c) = A + B \times (c/100) + C \times (c/100)^2 + D \times (c/100)^3$ and

A=+68.759, B=+124.77, C=−12.851, D=−10.095, where c is the present $CH_2O$ content of the aqueous formaldehyde solution during the evaporation in % by weight and is from 20 to 99% by weight.

The pressure in the course of evaporation is preferably 0.1 to 50 bar. The molar $CH_2O$ to $H_2O$ ratio is preferably ≥1.4. In addition, it is preferred to perform the evaporation in a stirred tank, a helical tube, a film evaporator or another apparatus with heat exchanger characteristics.

In step b) of the process according to the invention, the water is removed from the aminal obtained in step a). This establishes a water content of 0 to 5% by weight based on the aminal. The water is obtained firstly as the second main product in the aminal synthesis in step a), and is secondly present at least in traces in the reactant used in step a) (highly concentrated formaldehyde with a $CH_2O$ content of >50% by weight).

In step b), a water content of preferably 0.5 to 5% by weight, more preferably 1 to 4% by weight, based on the aminal, is established. The water content can be determined, for example, by the Karl-Fischer method, which is described, for example, in Jander, Jahr, Maβanalyse [Quantitative Analysis], 15th edition, de Gruyter, Berlin (1989), p. 289 to p. 292.

In step c) of the process according to the invention, an acidic catalyst is added to the aminal with a water content of 0 to 5% by weight.

The acidic catalysts used may be strong organic or strong inorganic acids. Suitable acids are, for example, hydrochloric acid (HCl), sulfuric acid, phosphoric acid and methanesulfonic acid. Preference is given to using aqueous hydrochloric acid in the process according to the invention. The aqueous hydrochloric acid is present typically in concentrations of 25 to 36% by weight. In one embodiment of the present invention, preference is given to using gaseous HCl.

Preference is given to adding the acidic catalyst in catalytic amounts. This means that, based on the aminal, a significantly smaller amount of catalyst is used. Consequently, in step c), a much smaller amount of water is introduced into the reaction system compared to step a) when the acidic catalyst is used in the form of an aqueous solution. As a result of the addition of the acidic catalyst, the above-described rearrangements of the aminal via the aminobenzylaniline intermediates to MDA can proceed. Since HCl is bound predominantly onto aniline and MDA, the specific amount of HCl used is calculated from the degrees of protonation specified. By means of the process according to the invention, 4,4'-MDA is prepared as the main product, and 2,4'-MDA and 2,2'-MDA as by-products, and possibly further higher homologs. The process according to the invention achieves the effect that MDA can be obtained in a weight ratio of the 2,4'-MDA to 4,4'-MDA isomers of between 0.05 and 0.15.

The acidic catalyst is added to the aminal with a water content of 0 to 5% by weight in step c) preferably by mixing, especially at temperatures of 20 to 60° C. The aminal with a water content of 0 to 5% by weight is mixed with the acidic catalyst preferably with a specific power input of >10 kW/m³ of mixing space, more preferably of >20 kW/m³ of mixing space. Preferably, after the addition of the acidic catalyst in step c), the aminal is rearranged (converted) to MDA at temperatures of 20 to 100° C. and/or at water contents of 0 to 20% by weight. In step c), the amount of acidic catalyst is selected such that a degree of protonation of <15%, preferably of 5 to 14%, more preferably of 6 to 13%, is established.

In a further embodiment of the present invention, the temperature of the reaction (rearrangement) can optionally be increased to values of 110 to 250° C. when the ratio of the proportions by weight of p-aminobenzylaniline to 4,4'-MDA in the acidic reaction mixture goes below a value of 1.00. The temperature of the reaction mixture can be increased in stages or continuously and optionally under elevated pressure. The temperature is preferably 110 to 180° C., especially 110 to 160° C. The aforementioned value which should not exceed the proportions by weight is preferably 0.50, more preferably 0.25 and especially 0.2.

Optionally, further substances, for example salts, (weak) organic or inorganic acids may be present in the process according to the invention. Optionally, the reaction product (MDA) obtained in the process according to the invention can be worked up further, for example by adding a base. Such workup steps are known to those skilled in the art.

The invention claimed is:

1. A process for preparing methylenediphenyldiamine (MDA), the process comprising:
    (a) converting formaldehyde and aniline to an aminal;
    (b) removing water from the aminal obtained in (a) to establish a water content of 0 to 5% by weight, based on the aminal; and
    (c) adding an acidic catalyst to the aminal having a water content of 0 to 5% by weight,
    wherein the formaldehyde in (a) is in the form of a first formaldehyde solution with a $CH_2O$ content of >50% by weight and is prepared by oxidative dehydrogenation from methanol.

2. The process claim 1, wherein the $CH_2O$ content of the first formaldehyde solution is ≥70% by weight.

3. The process of claim 1, wherein the first formaldehyde solution is in an aqueous solution or in gaseous form.

4. The process of claim 1, wherein the acidic catalyst in (c) comprises a strong organic acid or a strong inorganic acid.

5. The process of claim 4, wherein the strong inorganic acid comprises HCl.

6. The process of claim 1, wherein, after the adding of the acidic catalyst in (c), the aminal is rearranged to MDA at a temperature of 20 to 100° C. or at a water content of 0 to 20% by weight.

7. The process of claim 1, wherein aniline and formaldehyde are converted in (a) at a molar ratio of 1.5:1 to 6:1 and temperature of 20 to 100° C.

8. The process of claim 1, wherein the first formaldehyde solution in (a) is prepared from a second aqueous formaldehyde solution with a lower $CH_2O$ content by evaporating a portion of the second solution by heating the second aqueous formaldehyde solution to an evaporation temperature at which the water is enriched in the gas phase relative to the liquid phase, and the gas phase formed is drawn off continuously or discontinuously.

9. The process of claim 1, wherein the first formaldehyde solution in (a) is prepared from a second aqueous formaldehyde solution with a lower $CH_2O$ content by a process comprising:
    supplying the second aqueous formaldehyde solution with a lower $CH_2O$ content to a preheater;
    heating the second aqueous formaldehyde solution in the preheater, to obtain a heated solution;
    decompressing the heated solution with a pressure-retaining device, to obtain a decompressed solution; and
    concentrating the decompressed solution in a helical tube evaporator, to obtain a vapor stream and the first formaldehyde solution with a $CH_2O$ content of >50% by weight as a bottom stream.

10. The process of claim 1, wherein the first formaldehyde solution in (a) is stabilized against precipitation of a solid by heating it immediately after preparation thereof with a heating rate of at least 5° C./min to a temperature in a range of at least 80 to not more than 200° C., and storing it at a temperature in the range of at least 80 to not more than 200° C.

11. The process of claim 1, wherein gaseous formaldehyde with a $CH_2O$ content of >50% by weight and a molar $CH_2O$ to $H_2O$ ratio of >0.6 is employed in (a), and
   wherein the gaseous formaldehyde is prepared by evaporating at least a portion of a second aqueous formaldehyde solution.

12. The process of claim 8, wherein the $CH_2O$ content of the first formaldehyde solution is ≥70% by weight.

13. The process of claim 9, wherein the $CH_2O$ content of the first formaldehyde solution is ≥70% by weight.

14. The process of claim 10, wherein the $CH_2O$ content of the first formaldehyde solution is ≥70% by weight.

15. The process of claim 11, wherein the $CH_2O$ content of the first formaldehyde solution is ≥70% by weight.

* * * * *